United States Patent [19]

Dapra et al.

[11] Patent Number: 4,586,497
[45] Date of Patent: May 6, 1986

[54] DRILL FIXATION DEVICE AND METHOD FOR VERTEBRA CUTTING

[75] Inventors: David J. Dapra, 5501 Ambrose Dr., Reno, Nev. 89509; John B. Clementi, So. Milwaukee, Wis.; Robert J. Morelli, Reno, Nev.

[73] Assignee: David J. Dapra, Reno, Nev.

[21] Appl. No.: 546,968

[22] Filed: Oct. 31, 1983

[51] Int. Cl.$^4$ .................. A61F 5/04; A61F 17/32
[52] U.S. Cl. .................. 128/92 E; 128/305
[58] Field of Search ............ 128/92 R, 92 E, 92 EB, 128/305, 310, 305.1

[56] References Cited

U.S. PATENT DOCUMENTS

| | | | |
|---|---|---|---|
| 1,831,813 | 11/1931 | Levedahl | 128/92 EB |
| 2,547,707 | 4/1951 | Karle | 128/310 |
| 2,675,003 | 4/1954 | Veley | 128/310 |
| 3,049,018 | 8/1962 | Lusskin et al. | 128/310 |
| 3,308,828 | 3/1967 | Pippin | 128/310 |
| 3,384,085 | 5/1968 | Hall | 128/305.1 |
| 3,750,671 | 8/1973 | Hedrick | 128/305 |
| 3,835,860 | 9/1974 | Garretson | 128/310 |
| 3,867,932 | 2/1975 | Huene | 128/92 E |
| 4,071,031 | 1/1978 | Hedrick | 128/310 |
| 4,187,559 | 2/1980 | Grell et al. | 128/92 EB |
| 4,257,411 | 3/1981 | Cho | 128/92 EB |
| 4,312,337 | 1/1982 | Donohue | 128/310 |
| 4,364,381 | 12/1982 | Sher et al. | 128/92 EB |
| 4,444,180 | 4/1984 | Schneider | 128/92 EB |

OTHER PUBLICATIONS

British J. of Surg., vol. 25, 1937–1938, pp. 726–734, "The Evolution & Development of Surg. Instruments", by Thompson.

Primary Examiner—Gene Mancene
Assistant Examiner—C. W. Shedd
Attorney, Agent, or Firm—Limbach, Limbach & Sutton

[57] ABSTRACT

A drill fixation device (F) to adapt a high speed drill (D) for use in vertebra drilling and cutting. The device includes a carrier (16) mounting the drill (D) for guided movement relative to a base (14) and a squeeze grip (22-24) connected between the base (14) and carrier (16) to enable a surgeon to selectively impart such movement to the drill. A foot plate (50) is fixed relative to the base (14) in spaced relationship to the carrier (16) so as to be in the path of the bit (12) of a drill (D) mounted on the carrier (16). In use, the foot plate (50) is positioned beneath the bone material to be cut to apply counterforce to the bone material as the drill cuts and shield nerve tissue from harm by the bit.

13 Claims, 9 Drawing Figures

U.S. Patent  May 6, 1986  Sheet 1 of 2  4,586,497
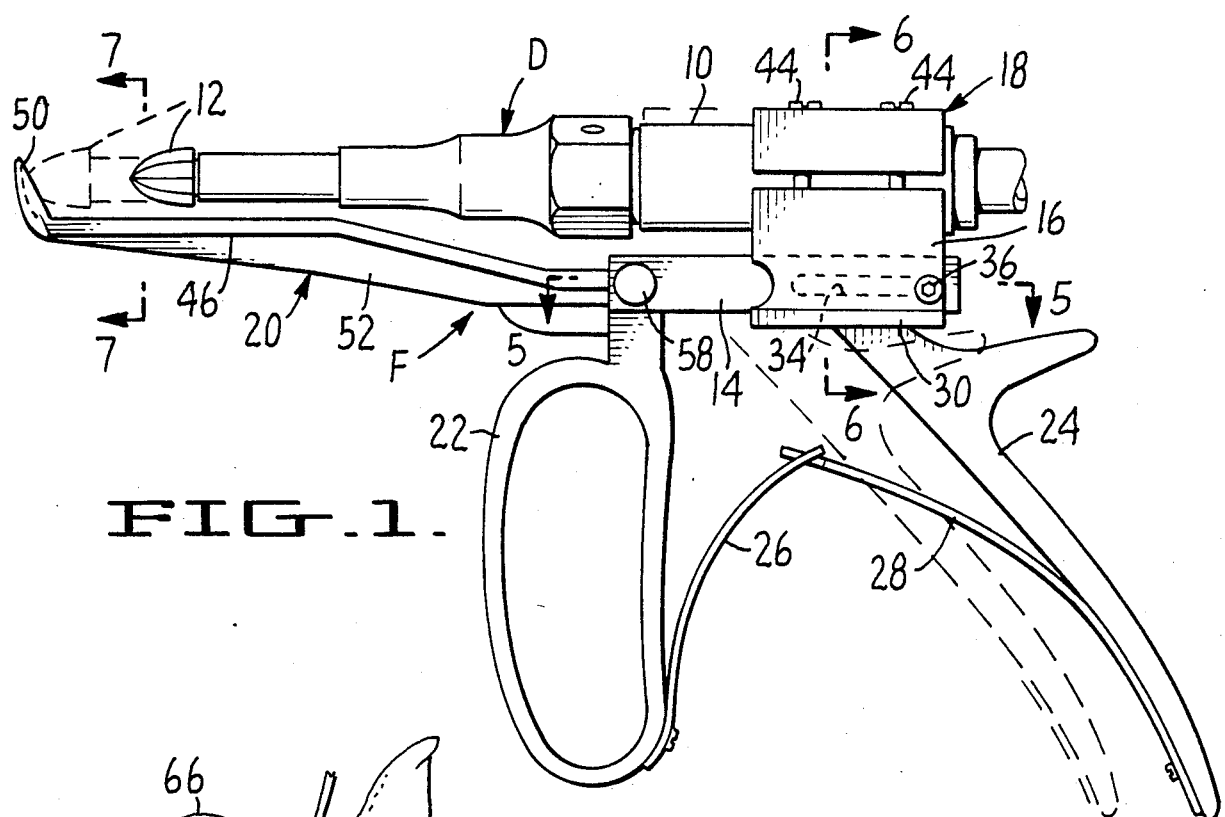
FIG. 1.
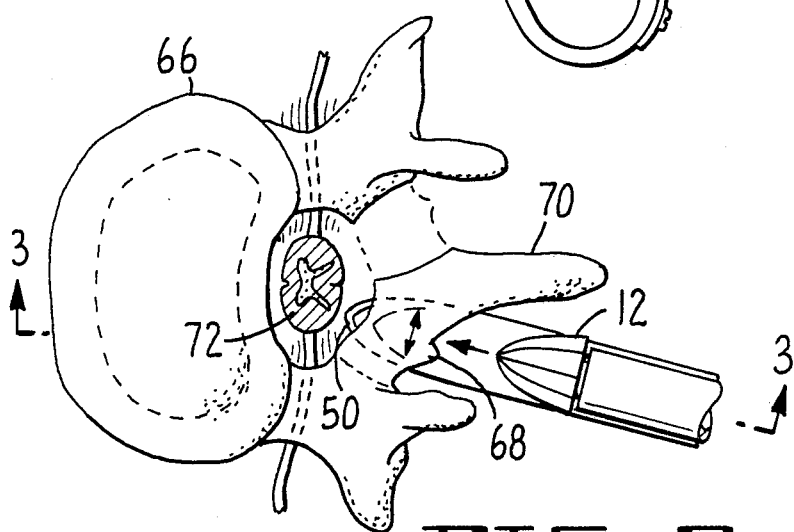
FIG. 2.
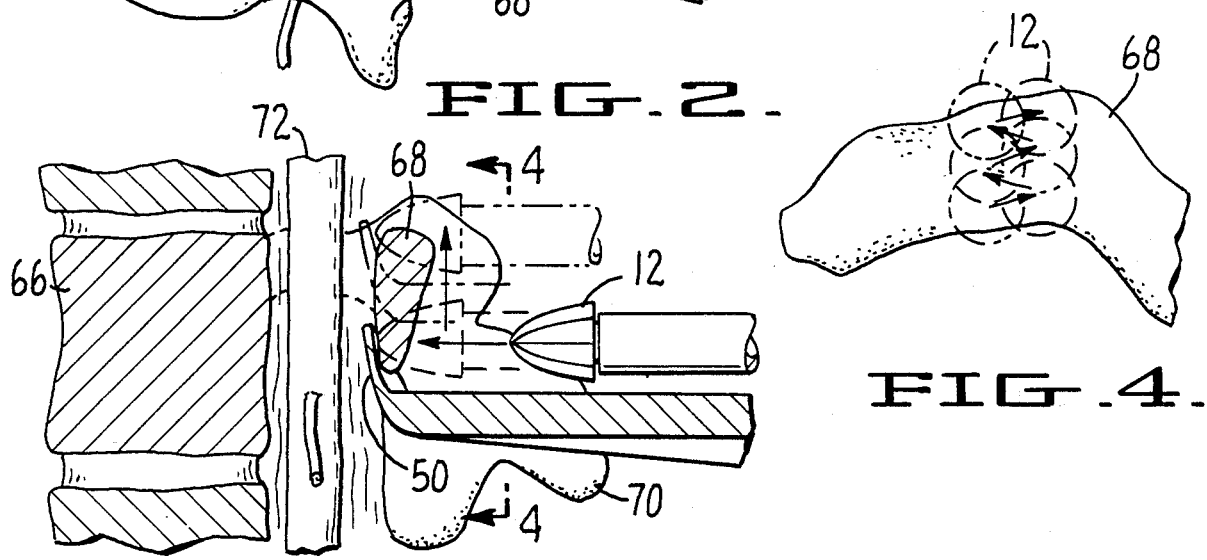
FIG. 3.
FIG. 4.

DRILL FIXATION DEVICE AND METHOD FOR VERTEBRA CUTTING

DESCRIPTION

BACKGROUND OF THE INVENTION

The present invention relates to a device to enable a high speed drill to be safely used around the spinal cord and nerve roots in the removal of bone material during the course of spinal surgery. It is particularly concerned with such a device which provides an advancing mechanism to precisely direct the drill in all planes of movement and a foot plate which is positioned beneath the bone material to be removed to shield the spinal cord and nerve roots and provide a counterforce to the cutting force applied through the drill.

The most common cutting tool used to remove bone material in spinal surgery is a cutting rongeur. Such devices employ a manual snipping action and are not power driven. They are somewhat similar to principle to the present invention, however, in that they employ a hooked end which is engaged beneath the material to be cut and a cutter which moves a guided path toward the hooked end.

The prior art also teaches surgical bone punches which function much like a conventional paper punch, and various types of cutters which employ saw or router-like elements which are shielded by foot or leg-like structures. In the latter devices, however, the foot or leg-like structures are stationary in relation to the cutting mechanism. They do not provide for movement of the cutting mechanism toward a foot plate which is engaged beneath the bone material being worked upon, and do not provide the precise control which is effected through means of the counterforce provided by the foot plate of the present invention.

SUMMARY OF THE INVENTION

The apparatus and method of the invention provides a foot plate which may be positioned beneath the bone material to be cut and a mounting to secure a rotationally driven drill bit for guided movement relative to the plate. In use, a squeezing force is used to move the bit along said path and into engagement with the bone material to be cut. Simultaneously with the application of the squeezing force, the foot plate is pulled against the bone material to apply a counterforce to the fixation device for the drill.

A principal object of the invention is to provide a fixation device and method for a high speed drill which enables the drill to be precisely directed in all planes of movement and shields nerve tissue from harm by the drill.

A more general object is to provide such a fixation device which facilitates and speeds the performance of foraminotomy and laminectomy operations.

Still another object is to provide a drill fixation device which provides for precise control of the drill by utilizing a foot plate which is engaged beneath the bone material to be cut and a squeezing mechanism which may be used to advance the drill toward the material as the foot plate applies the counterforce of the bone as a resistive force.

Yet another object related to the latter object is to provide such a device wherein the differential force resulting from the counterforce of the bone serves to control the cutting force applied to the drill.

The foregoing and other objects will become apparent when viewed in light of the following detailed description and accompanying drawings wherein:

BRIEF DESCRIPTION OF THE DRAWINGS

FIG. 1 is a side elevational view of the fixation device with a high speed air drill mounted therein;

FIG. 2 is a plan view of a vertebrae in the process of being cut for a laminectomy through means of the method and apparatus of the invention;

FIG. 3 is a cross-sectional view taken on the plane designated by line 3—3 of FIG. 2, with arrow lines and phantom illustrations showing the planes of movement through which the fixation device and the bit of a drill carried thereby move in the course of a laminectomy operation;

FIG. 4 is a cross-sectional view taken on the plane designated by line 4—4 of FIG. 3, with arrow lines and phantom illustrations showing the planes of movement through which a drill bit carried by the device moves in the course of a laminectomy operation;

DESCRIPTION OF THE PREFERRED EMBODIMENTS

Figure 5:
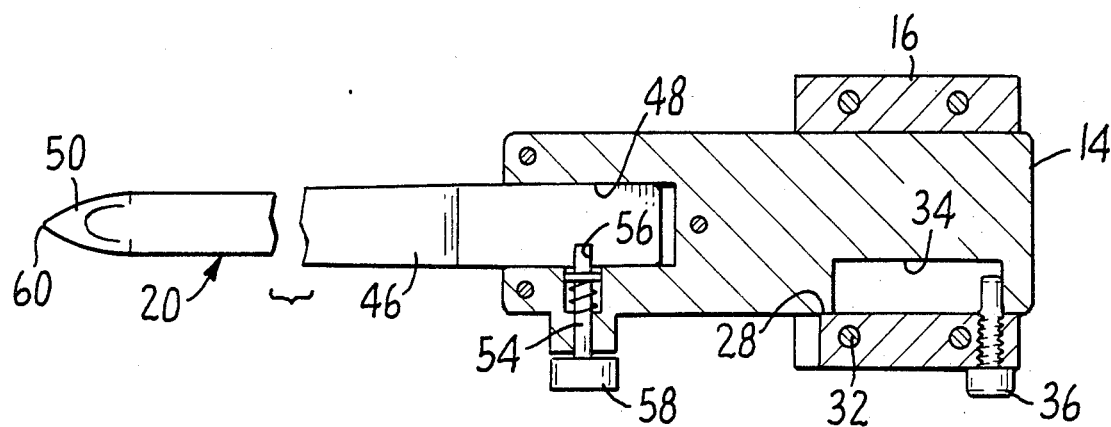
FIG. 5 is a transverse cross-sectional view taken on the plane designated by line 5—5 of FIG. 2.

Referring now to FIG. 1, the fixation device is designated by the letter "F" and is shown carrying high-speed air drill "D". The drill is of conventional construction and may, for example, be of the type manufactured by Midas Rex Pneumatic Tools of Fort Worth, Tex., and known as a WHIRLWIND BONE SCALPEL. It includes a stationary body 10 of hexagonal cross-section having a rotating drill bit 12 extending longitudinally from one end thereof. In the preferred embodiment illustrated, the bit 12 takes the form of an acorn-shaped burr.

The principal elements of the fixation device comprise: a base 14; a carrier 16 mounted on the base for guided rectilinear movement relative thereof; a clamp assembly 18 to secure the drill body 10 to the carrier 16; a foot plate assembly 20; and a squeeze grip assembly comprised of a finger grip 22 fixedly secured to the base 14 a palm grip 24 fixedly secured to the carrier 16. Interengaging leaf springs 26 and 28 are secured between the grips to resiliently bias the carrier 16 to the right, as viewed in FIG. 1, relative to the base 14.

Figure 6:
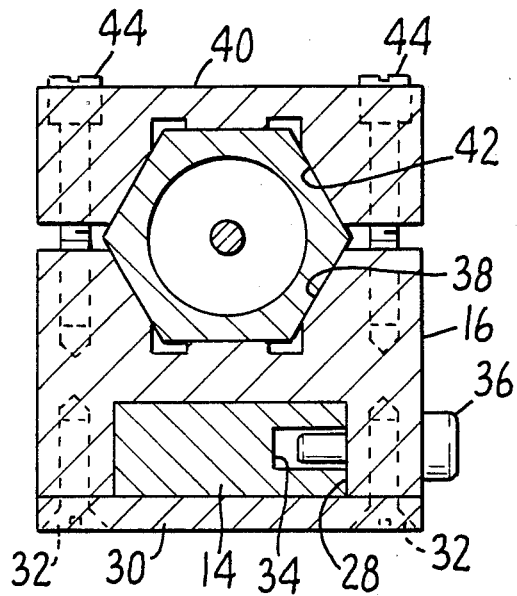
FIG. 6 is a transverse cross-sectional view taken on the plane designated by line 6—6 of FIG. 1.

As may be seen from FIG. 6, the base 14 is of generally rectangular cross-section and the carrier 16 is formed with a recess 28 complemental to and slidably received on the base. A plate 30 secured to the carrier by screws 32 captures the base 14 within the recess 28. Movement of the carrier 16 relative to the base 14 is limited through means of a groove 34 (see FIG. 1) formed to the side of the base 14 and a stop screw 36 threadably engaged in an opening therefor provided in the carrier 16 and slidably received within the groove 34.

The clamp assembly 18 comprises a recess 38 formed in the top of the carrier 16, a clamping plate 40 having a recess 42 formed therein, and four screws 44 extending through the plate 40 into threaded engagement with openings therefor provided in the carrier 16. The grooves 38 and 42, as may be seen from FIG. 6, are shaped to complementally engage and clamp the hexagonal surfaces on the drill body 10. It should be understood that the shape of these grooves could be varied to accomodate drill bodies of different shapes.

Figure 7:
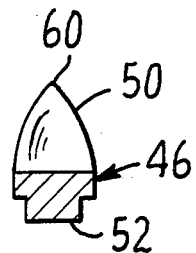
FIG. 7 is a transverse cross-sectional view taken on the plane designated by line 7—7 of FIG. 1.

The foot plate assembly 20 comprises an extension 46 releasably engaged in a socket 48 provided therefor in the base 14, and a foot plate 50 extending upwardly from the distal end of the extension 46 in a position disposed in the longitudinal path through which the drill bit 12 moves responsive to movement of the carrier 16 relative to the base 14. The extension 46 is of a cruciform cross-section (see FIG. 7) and includes a reinforcing web 52. The proximal end of the extension which is received in the socket 48 is releasably fixed to the base 14 through means of a spring biased detent pin 54 carried by the base member and a recess 56 formed in the extension. As shown in FIG. 5, the pin 54 complementally engages the recess 56 to lock the extension 46 to the base. Release is effected by simply pulling the pin 54 outwardly through means of the knob 58 formed thereon.

The foot plate 50 is of relatively thin cross-section and concave on the inside thereof facing the bit 12. The plate terminates in a thin edge 60 at the distal end thereof. In the preferred embodiment shown, the plate extends at about 10 to 20 degree angle relative to the extension 46.

Figure 8:
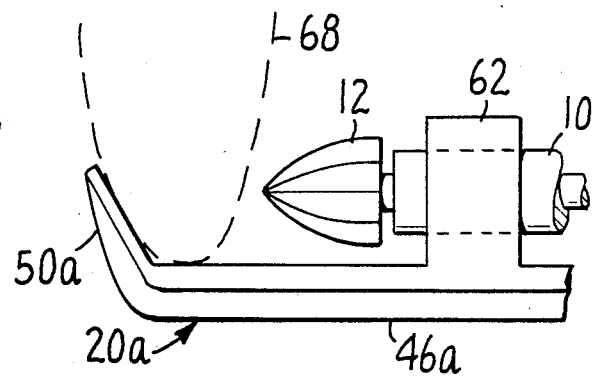
FIG. 8 is a side elevational partial view of a modified foot plate for engagement beneath a bone segment, with a phantom line illustration showing a bone segment positioned for cutting.

The modified foot plate assembly of FIG. 8 is designated by the numeral 20a. It differs from that of FIG. 1 primarily in that an arch 62 thereon slidably receives the end of the drill body 10 to further secure the drill body against lateral displacement relative to the extension 46a. The foot plate 50a of the FIG. 8 embodiment corresponds to that of the FIG. 1 embodiment.

Figure 9:
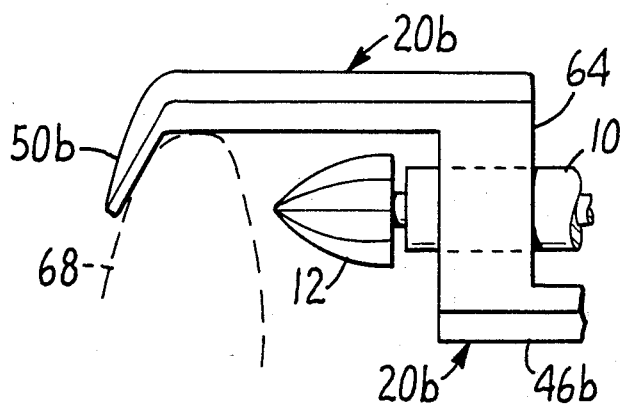
FIG. 9 is a side elevational partial view of a modified foot plate designed for engagement over a bone segment, with a phantom line illustration showing a bone segment positioned for cutting.

The modified foot plate assembly of FIG. 9 is designated by the numeral 20b. It differs from that of the FIG. 1 embodiment in that an arch 64 extends upwardly from the extension 46b and that the distal end of the extension extends from the upper end of the arch and over the drill bit. The arch 64 slidably receives the drill body 10 and, similarly to the arch 62 of the FIG. 8 embodiment, serves to secure the extension of the foot plate assembly against lateral displacement relative to the drill. The foot plate 50b of the FIG. 9 embodiment is similar to that of the FIG. 1 embodiment with the exception that it extends downwardly, rather than upwardly.

The operation of the invention may be seen from FIGS. 2, 3 and 4 wherein a vertebral body 66 is shown in the process of having a laminectomy performed thereon. There it will be seen that the drill is in the process of cutting the lamina 68 to one side of the spinous process 70. As seen in these figures, the foot plate 50 is beneath the lamina 68 and serves to shield the spinal cord 72. It also, through the pulling force applied thereto by the surgeon, applies a counterforce to the lamina as the drill is moved longitudinally into the bone material being cut by squeezing of the grips. The arrow lines in FIGS. 3 and 4 show the path through which the drill bit is moved to cut away the desired section of lamina.

It should be appreciated that the surgeon naturally tends to pull the fixation device away from the vertebral body as he applies squeezing force to move the drill bit into cutting engagement with the bone. This pulling force imparts a counterforce to the fixation device through the bone of the lamina being cut. It also, in the event of slippage, results in pulling of the fixation device and the drill carried thereby away from the cutting site, rather than towards it.

FIGS. 8 and 9 also show the devices therein in the process of cutting a portion of lamina 68. As shown in FIG. 8, the lamina is essentially in the same position as that illustrated in FIGS. 2 to 4. As illustrated in FIG. 9, the lamina is beneath the foot plate 50b. Thus, cutting with the FIG. 9 embodiment is achieved in a downwardly direction relative to the bone being worked upon.

It should be appreciated that the surgeon would grip the fixation device with his fingers through the grip 22 and the palm or heel of his hand against the grip 24. Manipulation in this way would be achieved with one hand, leaving the surgeon's other hand free for body support or other manipulation.

While preferred embodiments have been illustrated and described, it should be understood that the invention is not intended to be limited to the specifics of these embodiments, but rather is defined by the accompanying claims. It should also be understood that the invention may find use in foraminotomies as well as other types of surgery where bone cutting is necessary.

What is claimed is:

1. A device to position a high-speed rotary bone cutter relative to the bone tissue being cut, said device comprising:
    a base having a first grip attached thereto;
    a carrier with a fixture means for securing a rotary cutter thereto;
    mounting means connecting said base and said carrier for guided relative movement therebetween;
    a second grip, connected to the carrier and cooperating with said first grip to enable an operator of the device to selectively impart said movement by squeezing said first and second grips;
    a foot plate fixedly connected to said base and engageable with bone tissue to be cut to place said tissue in the path of said rotary cutter between the cutter and the plate, and wherein squeezing said grips impinges said cutter on said tissue when so placed.

2. A device according to claim 1 wherein said mounting means connects the carrier to the base for rectilinear movement towards and away from the foot plate and includes a stop to limit movement away from the foot plate.

3. A device according to claim 1 wherein the first grip comprises a finger engageable portion fixed to and extending generally perpendicular from the base and said second grip is in apposition to the first grip and adapted to be engaged by an operator's palm.

4. A device according to claim 3 further comprising means resiliently biasing the first and second grips apart.

5. A device according to claim 1 wherein said foot plate is carried by an extension connected to and extending generally parallel to the path of said guide movement.

6. A device according to claim 5 wherein the extension has a distal end proportioned to extend adjacent said cutter and the foot plate extends from said end toward the path of said guided movement.

7. A device according to claim 5 further comprising means to selectively release the extension from the base to enable the foot plate to be removed from the base.

8. A device according to claim 5 wherein the foot plate converges to a thin distal edge.

9. In combination with a motor having a stationary body with a rotationally driven bit extending from one end thereof, a rotary cutting device comprising: a carrier fixedly secured to said body in a disposition wherein the bit extends longitudinally relative thereof; a base; means mounting the carrier on the base for guided longitudinal movement relative thereto; a squeeze grip connected between the base and carrier to impart said relative movement to the carrier; and a foot plate connected to the base in spaced relationship to the carrier and the bit, said foot plate being aligned with the path through which the bit moves upon longitudinal movement of the carrier relative to the base so as to impinge said bit into a workpiece entrapped between said foot plate and bit.

10. A combination according to claim 9 wherein said foot plate is carried by an extension connected to and extending generally parallel to the path of said guided movement.

11. A combination according to claim 10 wherein the foot plate converges to a thin distal edge.

12. A method of cutting bone tissue comprising the steps of:
mounting a rotationally driven cutter bit for guided movement toward a foot plate,
providing squeezable means for actuating said guided movement,
positioning said bone tissue in engagement with said foot plate within the extent of said guided movement,
and manually squeezing said squeezable means to advance said rotating cutter bit into engagement with said bone tissue and thereby cutting same.

13. A method according to claim 12, further comprising the step of applying a retaining force simultaneously with the step of squeezing, and retaining force comprising pulling said foot plate against the tissue to be cut to thereby reduce any tendency of said foot plate to slip from engagement with said bone tissue.

* * * * *